(12) United States Patent
Burstein

(10) Patent No.: US 6,500,386 B1
(45) Date of Patent: Dec. 31, 2002

(54) METHOD FOR PRESERVING STERILIZED IMPLANT COMPONENTS

(76) Inventor: Albert H. Burstein, 636 Mourning Dove Dr., Sarasota, FL (US) 34236

(*) Notice: Subject to any disclaimer, the term of this patent is extended or adjusted under 35 U.S.C. 154(b) by 0 days.

(21) Appl. No.: 09/185,567

(22) Filed: Nov. 4, 1998

(51) Int. Cl.[7] .............................. A61L 2/00; B01J 19/00; G05B 1/00

(52) U.S. Cl. .......................... 422/22; 422/28; 422/40; 422/105; 422/299

(58) Field of Search ............................. 422/22–23, 28, 422/40, 105, 108, 292, 299

(56) References Cited

U.S. PATENT DOCUMENTS

| | | | | |
|---|---|---|---|---|
| 5,190,724 A | * | 3/1993 | Hachmann et al. | 422/28 |
| 5,577,368 A | * | 11/1996 | Hamilton et al. | 53/432 |
| 5,759,486 A | * | 6/1998 | Peterson | 422/21 |
| 6,030,530 A | * | 2/2000 | Esposito et al. | 210/321.6 |
| 6,039,921 A | * | 3/2000 | Boucher | 422/21 |

OTHER PUBLICATIONS

Perry's Chemical Engineering Handbook, Sixth Edition.*
Li, S. and Burstein, A. H; Ultra–High Molecular Weight Polyethylene, The material and its uses in total joint implants. J. Bone and Joint Surge. 76–A: 1080–1090, 1994.
Eyerer, P.: Property Changes of Ultra–High Molecular Weight Polyethylene, during implantation. Trans. Soc. Biomater., 8: 184, 1985.
Eyerer, P., and Ke, Y.C.: Characterization of UHMW Polyethylene Hip cups run on joint simulators, J. Biomed. Mater. Res., 21: 275–291, 1987.
Nusbaum, H.J., and Rose, R.M.: The Effects of Radiation Sterilization on the Properties of Ultra–highmolecular Weight Polyethylene, J. Biomed. Mater. Res., 13: 557–576, 1979.
Rimnac, C.M.:, Klein, R.W.; Betts, F.; and Wright, T.M.; Post–irradiation aging of ultra–high molecular weight polyethylene. J. Bone and Joint Surg., 76–A: 1052–1056, 1994.
Rimnac, C.M.; Wright, T.M.; Klein, R.W.; Betts, F.; and Schapiro, E.: Characterization of material properties of ultra–high molecular weight polyethylene before and after Implantation. Trans. Soc. Biomat. implantation Retrieval Smmpos., 15: 16, 1992.

* cited by examiner

*Primary Examiner*—Robert J. Warden
*Assistant Examiner*—Monzer R. Chorbaji
(74) *Attorney, Agent, or Firm*—Richard J. Danyko, Esq.; Michael A. Nicodema, Esq.; Dreier & Baritz LLP

(57) ABSTRACT

A method for preserving a component including polymeric material that reduces oxidation degradation after irradiation. The method includes sealing the polymeric material in a container filled with a fluid, preferably a liquid. Monitoring the integrity of the container's seal is enhanced by use of liquid rather than a gas. The method can be used for long term storage of orthopaedic implants which include polymeric material, especially Ultra High Molecular Weight Polyethylene.

20 Claims, 3 Drawing Sheets

METHOD FOR PRESERVING STERILIZED IMPLANT COMPONENTS

FIELD OF THE INVENTION

The present invention relates to a method of preserving sterilized implant which contains polymeric components, and the sterilized sealed package which contains a quench liquid reducing free radical generation and oxidative degradation, an implant, and an optional leak indicator. More particularly, the present invention provides a method for producing stable implants by reducing free radical generation and oxidative degradation of implants formed from or containing ultra high molecular weight polyethylene (UHMWPE), while at the same time, permitting cross-linking of the polymer component.

BACKGROUND OF THE INVENTION

Human and animal implant components generally must be sterilized before implantation. A common sterilization approach is irradiation, especially gamma irradiation. However, irradiation can adversely affect the implant component.

In particular, gamma irradiation can adversely affect orthopaedic implant components made from or including polymeric materials. Irradiated polymeric materials typically exhibit an increased oxidation rate which is thought to be due to the formation of free radicals during irradiation. Oxidation may continue during storage after sterilization is complete. Implant oxidation can result in decreased ductility, higher wear rates, and shorter functional life.

Oxidation can be reduced in some cases by sealing the implant component in an air-tight/water-tight container before sterilization and removing the implant component from the container shortly before implantation. The container is typically filled with an inert gas or is maintained under a vacuum to prevent oxidation. Likewise, an oxygen absorbent material can be placed inside the container to remove oxygen.

However, if the container seal is compromised, undetected oxygenation can occur. Another problem is that filling a container with a gas and subsequent sealing is complex. Upon sealing, the gas diffusion rate of the container limits the shelf-life of the sealed component as oxygen from the surrounding air diffuses into the container.

Hence, one problem with preserving implant components, particularly those containing polymeric materials, is limited shelf-life. Another is undetected container breach which reduces the functional life of the implant component.

SUMMARY OF THE INVENTION

The present invention provides a method of preserving polymeric materials after sterilization and before implantation such that free radical generation are minimized, and the packaged containers in which the method can be carried out and stored after sterilization.

One aspect of the present invention is a method of sterilizing which reduces free radical generation and oxidative degradation of implants formed from or containing polymeric materials, permits cross-linking of the polymer component, and increases shelf-life of the sterilized implant.

Another aspect of the present invention is providing a packaged implant for sterilization with sufficient quench liquid for sterilization and to avoid formation of a dry surface on the packaged implant.

A still further aspect of the present invention is preserving an polymer containing implant by contacting the component with a free radical quenching fluid in a closed environment, and sterilizing the in the presence of radiation in the presence of the free radical quenching fluid.

A further aspect of the present invention is providing a sealed and sterilized package, e.g., an article of manufacture, which includes (i) a fluid impermeable, sealed, radiation transparent container, (ii) a free radical quenching liquid within the container, and (iii) an implant component including a polymeric material, the liquid and implant component being sealed in the sealed container.

These aspects and other objects and advantages will become more apparent when considered in conjunction the following non-limiting detailed description, appended drawings and the claims.

DETAILED DESCRIPTION OF THE PRESENT INVENTION

In accordance with the present invention, an unsterilized implant containing or being formed from polymeric material, such as any biocompatible polymer, e.g., ultra-high molecular weight polyethylene (UHMWPE), is sterilized and stored before use. This invention applies equally to other biocompatible polymeric materials such as polypropylene, high density polyethylene, polyester, nylon, polyurethane, silicone, and similar materials and any other biocompatible material that may be used in the manufacture of biomedical implants.

The polymeric material is usually formed from polymer resin powder that is ram extruded or compression molded. Additional machining of the polymeric material alone or in combination with other materials may be required to complete the implant. Once the implant is assembled, it should be sterilized before being stored or used. A common use for such polymeric materials is as medical implants, especially in biomedical and orthopaedic applications.

Figure 1:
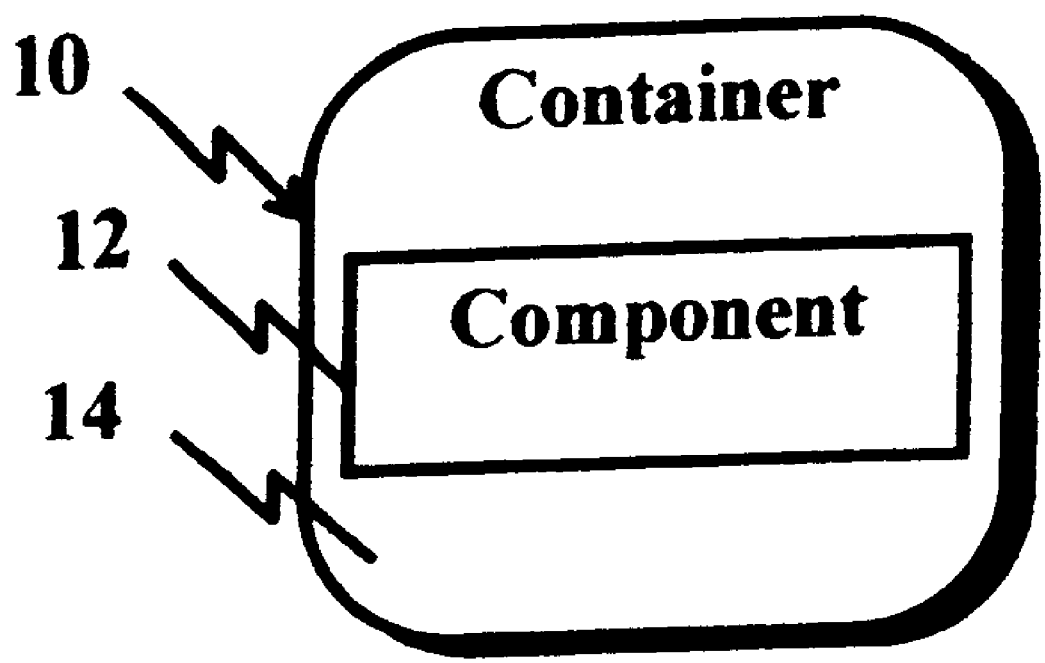
FIG. 1 depicts the packaged article prior to or subsequent of the sterilization process.

In FIG. 1, the ultra high molecular weight polyethylene (UHMWPE) component 12 is in container 10 which is filled with a fluid 14. Fluid 14 is generally a liquid such as water, aqueous alcoholic solutions, an alcohol or other suitable liquid which is a free radical quenching fluid. Suitable alcohols include methanol, ethanol or propanol. In one embodiment of the invention the fluid 14 is water. The fluid 14 is present in the container in an amount sufficient to maintain the surface of the implant wet. In otherwords, it is advantageous to use sufficient liquid in the container so that dry surfaces are not formed on the implant.

Suitable containers or packages should be air tight (gas impermeable) and liquid tight, and withstand a wide temperature range so that the container is not damaged during irradiation or storage. The container walls can be formed from a suitable material, such as polyethylene terephthalate, polyethylene vinyl alcohol and aluminum foil, or multi-layered compositions, such as polyethylene vinyl alcohol and polypropylene compositions.

The container 10 is transparent to radiation to permit component 12 within the container 10 to be sterilized. The container 10 is sealable by techniques known to those skilled in the art, such as, but not limited to a heat seal, a re-useable seal, which provides a dependable air-tight and liquid-tight seal.

In one embodiment, the component 12 is ultra-high molecular weight polyethylene (UHMWPE) having a weight average molecular weight of greater than $3.1 \times 10^6$ g/mole as measured by a relative viscosity of 2.30 or greater according to ASTM D 4020-96. The component 12 can be an assembled orthopaedic implant device. The fluid 14 should be a free radical quenching fluid. The fluid 14 is a liquid, preferably pure water or ethanol.

Figure 2:
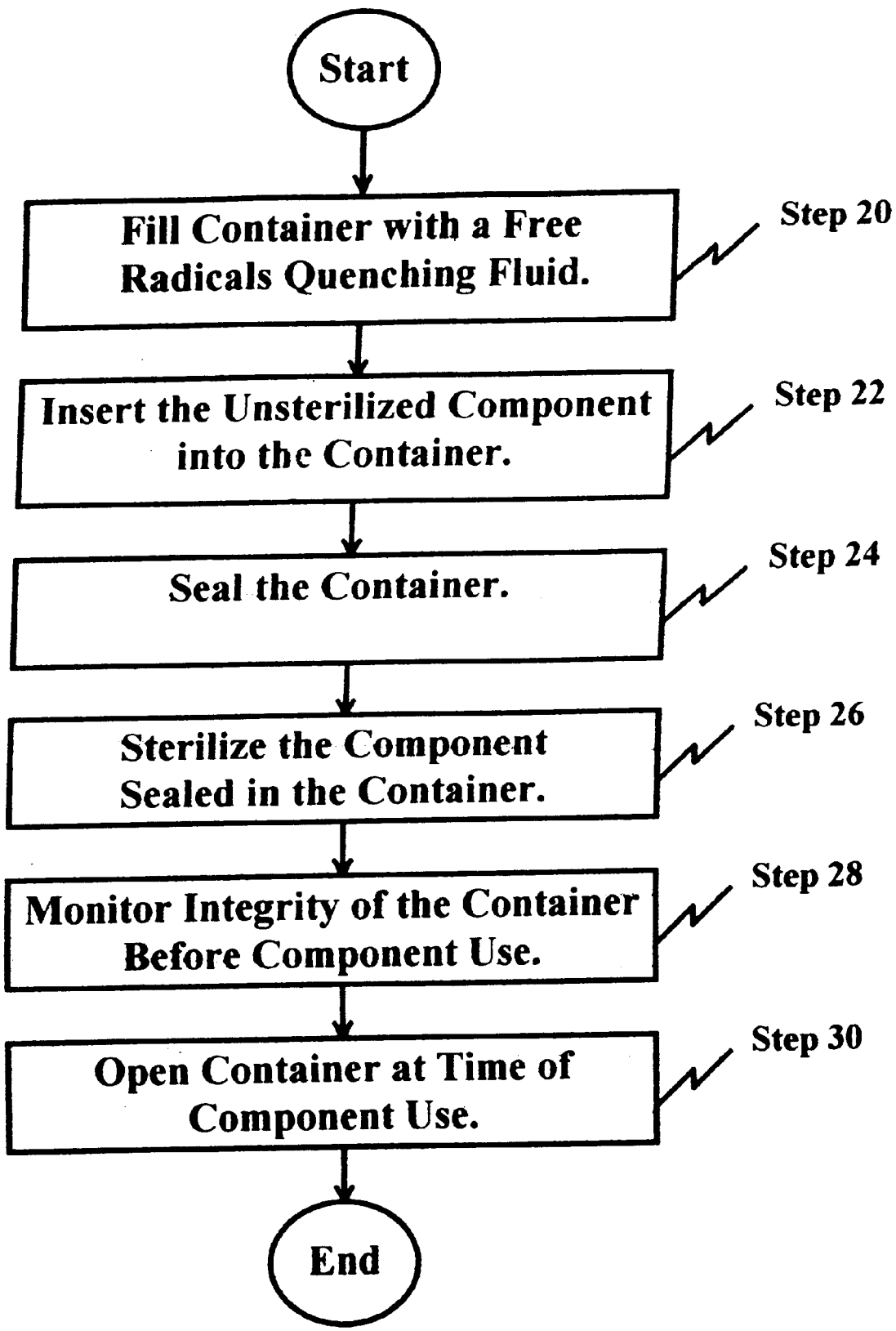
FIG. 2 is a flow diagram representing the preservation method for components including polymeric material.

In FIG. 2, the steps are illustrated for preserving a polymeric material after sterilization and before use, such that free radicals and thus oxidation are decreased.

As shown in FIG. 2, in step 20, a container 10, suitable for storing polymeric material 12, is filled with a free radical quenching fluid 14. In step 22, the unsterilized component 12 is placed in the container 10 filled with the free radical quenching fluid 14. In step 24, the container 10 is sealed. In step 26, the component 12 is sterilized. Sterilization can include any suitable radiation, especially gamma radiation, x-ray, and electron beam radiation. In step 28, the sealed container 10 with the now sterilized component 12 is stored for later usage. The integrity of the seal is monitored by detecting leakage of the free radical quenching fluid 14 from the container 10 by Drierite or similar water sensitive color changing material if the fluid is water. In step 30, the container 10 is opened shortly before or at the time the component 12 is to be used. Thus, the exposure of components 12 to air before implantation is minimized.

Two test specimens T-1 and T-2 were prepared from extruded and machined UHMWPE. The resin was manufactured by Hoechst Celanese and extruded by Poly Hi Solidur. The material had a tensile modulus of 916 MPa, a tensile yield of 24 MPa, an elongation to break of 390%, an ultimate tensile strength of 49 MPa, a density of 0.9316, a crystallinity of 59% and a melting point of 135.6° C.

Specimen T-1 was packaged using a conventional double seal technique. The packaged specimen was sterilized by a conventional gamma ray sterilization method using a 2.5 to 4.0 mega rads radiation dose.

Specimen T-2 was packaged in a similar manner except the inner package was filled with deionized water after the specimen was inserted and sealed by a heat seal. The test specimens were then removed from the packages and placed in water for 30 days. They were then placed in a glass chamber at 80° C., 100% humidity and 1 atmosphere of commercially pure $O_2$ for 10.5 days. Density, which is a direct measurement of the severity of oxidation as a function of depth, see references 1–6, was obtained as follows.

A core plug was removed from each specimen T-1 and T-2, and transversely sliced using a microtome. The density of the sliced material was determined using a standard water-propanol density column. The depth of each slice was known by setting the microtome to cut constant thickness slices and counting the slices.

Figure 3:
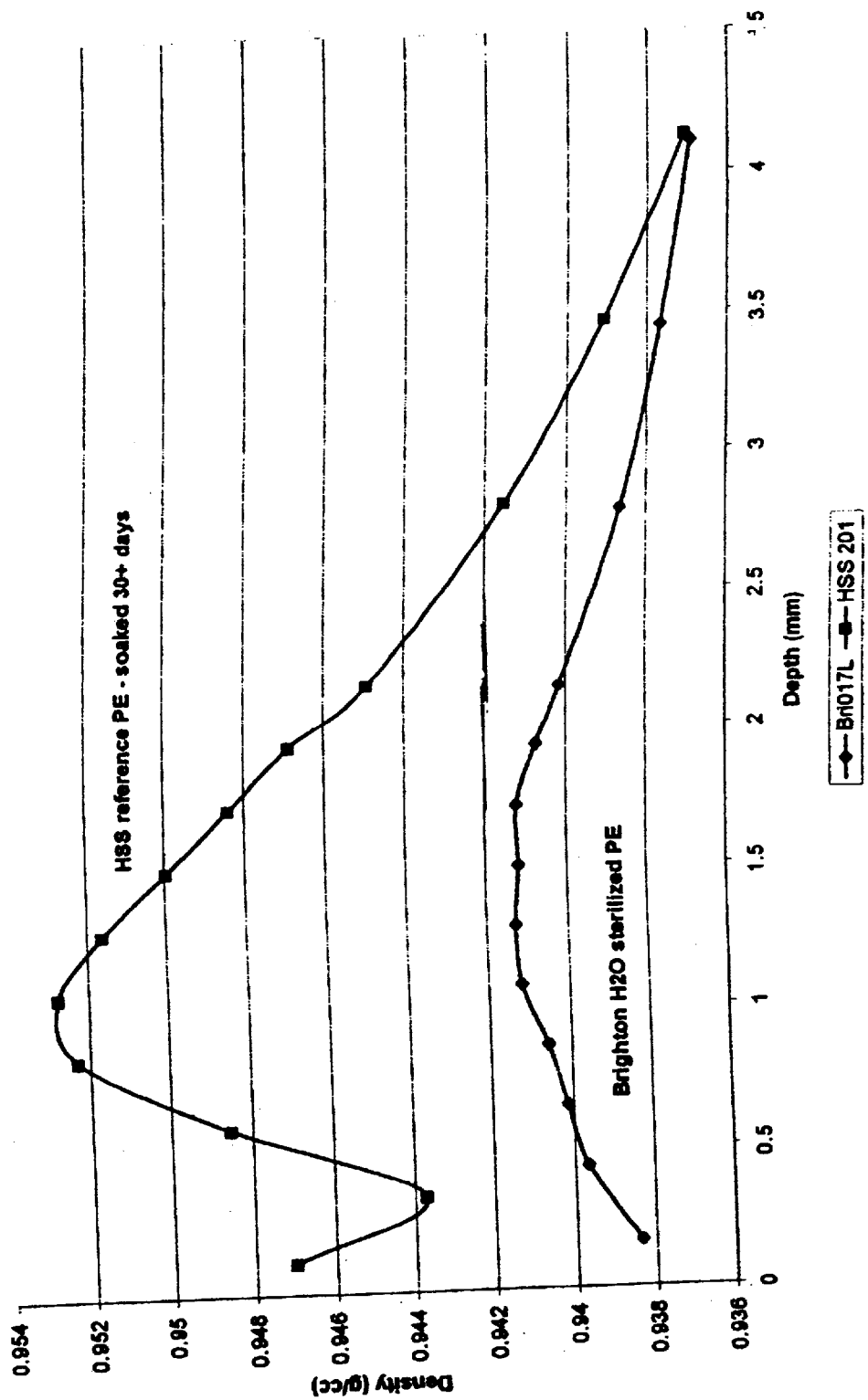
FIG. 3 is a graph depicting the effects of sterilization on various polyethylene samples.

The results are shown in Tables T-1, T-2 and the graph of FIG. 3.

COMPARATIVE EXAMPLE

TABLE T-1

| DEPTH (mm) | DENSITY (g/cc) |
|---|---|
| 0.112 | 0.9470 |
| 0.337 | 0.9437 |
| 0.592 | 0.9485 |
| 0.847 | 0.9523 |
| 1.072 | 0.9528 |
| 1.293 | 0.9516 |
| 1.511 | 0.9500 |
| 1.730 | 0.9484 |
| 1.949 | 0.9469 |
| 2.165 | 0.9449 |
| 2.820 | 0.9415 |
| 3.471 | 0.9391 |
| 4.126 | 0.9371 |

EXAMPLE OF THE PRESENT INVENTION

TABLE T-2

| DEPTH (mm) | DENSITY (g/cc) |
|---|---|
| 0.163 | 0.9384 |
| 0.435 | 0.9397 |
| 0.649 | 0.9401 |
| 0.863 | 0.9406 |
| 1.079 | 0.9412 |
| 1.292 | 0.9413 |
| 1.506 | 0.9412 |
| 1.722 | 0.9412 |
| 1.937 | 0.9408 |
| 2.148 | 0.9402 |
| 2.792 | 0.9387 |
| 3.449 | 0.9377 |
| 4.105 | 0.9370 |

As seen from the above data and FIG. 3, the present invention markedly reduces oxidation in the first 4 millimeters of the part thickness, the region where post-radiation normally occurs.

While the invention has been disclosed in a preferred embodiment, various modifications may be made therein by those skilled in the art without departing from the spirit and scope of the invention, as defined in the appended claims.

REFERENCES

1. Li, S. and Burstein, A. H; Ultra-high molecular weight polyethylene, the material and its uses in total joint implants. *J. Bone and Joint Surge.* 76-A: 1080–1090, 1994.
2. Eyerer, P.: Property changes of ultra-high molecular weight polyethylene, during implantation. *Trans. Soc. Biomater.*, 8:184, 1985.
3. Eyerer P., and Ke, Y. C.: Property changes of UHMW Polyethylene hip endoprostheses during implantation. *J. Biomed. Mater. Res.*, 21: 275–291, 1987.
4. Nusbaum, H. J., and Rose, R. M.: The effects of radiation sterilization on the properties of ultra-high molecular weight polyethylene. *J. Biomed. Mater. Res.*, 13: 557–576, 1979.
5. Rimnac, C. M.:, Klein, R. W.; Betts, F.; and Wright, T. M.; Post-irradiation aging of ultra-high molecular weight polyethylene. *J. Bone and Joint Surg.*, 76-A: 1052–1056, 1994.
6. Rimnac, C. M.; Wright, T. M.; Klein, R. W.; Betts, F.; and Schapiro, E.: Characterization of material properties of ultra-high molecular weight polyethylene before and after implantation. *Trans. Soc. Biomat. Implantation Retrieval Smmpos.*, 15: 16, 1992.

What is claimed is:

1. A method of preserving a component containing polymeric material, the method comprising the steps of:
   (a) contacting the component with a free radical quenching liquid in a closed environment, and
   (b) sterilizing, by radiation the component of step (a), while in the presence of the free radical quenching liquid.

2. The method of claim 1 wherein the closed environment is a sealable container comprising a radiation transparent material.

3. The method of claim 2, wherein the sealable container is visually transparent.

4. The method of claim 1, wherein the polymeric material is ultra high molecular weight polyethylene.

5. The method of claim 4, wherein the component is a medical implant device.

6. The method of claim 1, wherein the liquid is a solution.

7. The method of claim 1, wherein the liquid is a contains a $C_1$–$C_3$ alcohol.

8. The method of claim 7, wherein the liquid is a $C_1$–$C_3$ alcohol.

9. The method of claim 1, wherein the radiation is electro beam, gamma, or x-ray.

10. The method of claim 9 wherein the radiation is gamma.

11. The method of claim 1 further comprising the step of:
    (c) monitoring the integrity of the closed environment by detecting loss of the liquid.

12. A sterilized, sealed article comprising:
    (i) a liquid impermeable, sealed, radiation transparent container;
    (ii) a free radical quenching liquid within the container; and,
    (iii) an implant component comprising a polymeric material, wherein said liquid and implant component are sealingly maintained within said contained and said liquid wets the implant component.

13. The sterilized article of claim 12, wherein the polymeric material is ultra high molecular weight polyethylene.

14. The sterilized article of claim 13, wherein the component is a medical implant device.

15. The sterilized article of claim 12, wherein the liquid contains ethanol.

16. The sterilized article of claim 12, wherein the liquid is water.

17. The sterilized article of claim 12, wherein the liquid comprises an aqueous solution.

18. The sterilized article of claim 17, wherein the aqueous solution contains $C_1$–$C_3$ alcohol.

19. The sterilized article of claim 12, wherein the radiation is electro beam, gamma, or x-ray.

20. The sterilized article of claim 12, further including an indicator for monitoring the integrity of the closed environment by detecting loss of the liquid.

* * * * *